United States Patent [19]

Steer et al.

[11] Patent Number: 5,226,564
[45] Date of Patent: Jul. 13, 1993

[54] MANUFACTURE OF BAGS

[75] Inventors: Peter L. Steer; Graham E. Steer, both of Reigate, England

[73] Assignee: E. R. Squibb & Sons, Inc., Princeton, N.J.

[21] Appl. No.: 638,227

[22] Filed: Jan. 4, 1991

Related U.S. Application Data

[60] Division of Ser. No. 374,415, Jun. 30, 1989, Pat. No. 5,002,623, which is a division of Ser. No. 215,835, Jul. 6, 1988, Pat. No. 4,876,788, which is a continuation-in-part of Ser. No. 123,428, Nov. 20, 1987, abandoned.

[30] Foreign Application Priority Data

Nov. 28, 1986 [GB] United Kingdom ............... 8628480
Nov. 28, 1986 [GB] United Kingdom ............... 8628481
Jul. 8, 1987 [GB] United Kingdom ............... 8716089

[51] Int. Cl.$^5$ ..................... B65D 35/10; B65D 35/28
[52] U.S. Cl. ................................. 222/107; 222/566; 383/107; 383/906; 604/317; 604/408
[58] Field of Search ............... 222/107, 215, 527–530, 222/536, 566; 383/96, 904, 906, 3, 107; 604/317, 327, 335, 408

[56] References Cited

U.S. PATENT DOCUMENTS

| | | | |
|---|---|---|---|
| 3,007,608 | 11/1961 | Cox, Jr. ................ | 222/107 X |
| 3,173,579 | 3/1965 | Curie et al. ............. | 222/107 X |
| 3,589,506 | 6/1971 | Ford .................... | 383/96 X |
| 4,126,167 | 11/1978 | Smith et al. ............ | 604/317 |
| 4,300,560 | 11/1981 | Steer et al. ............ | 604/335 |
| 4,618,994 | 10/1986 | Bishop ................. | 383/906 X |
| 4,641,362 | 2/1987 | Muller ................. | 383/906 X |
| 4,650,452 | 3/1987 | Jensen ................. | 383/906 X |

FOREIGN PATENT DOCUMENTS

| | | | |
|---|---|---|---|
| 1445658 | 10/1966 | France ................ | 604/317 |
| 1308519 | 2/1973 | United Kingdom ......... | 222/107 |
| 2199500 | 7/1988 | United Kingdom ......... | 222/107 |

Primary Examiner—Donald T. Hajec
Attorney, Agent, or Firm—Stuart E. Krieger

[57] ABSTRACT

A synthetic plastic bag for containing liquids, e.g., urine, has a plastic outlet tube. It is manufactured by a first step of seam welding the tube between two superposed bag walls. In a subsequent step, an encircling sleeve is slide over the tube to a position where it contains within it the portions of the bag walls on either side of the tube. Thirdly, this sleeve is compressed onto the tube by a crimping operation conducted with the crimping force applied in a direction radially of the tube but at substantially right angles to the plane in which the bag walls lie. Alternatively, after the tube is seam welded between the bag walls, the bag and tube combination is then placed between the blocks of a mold, each block having confronting recesses of a particular shape and molten plastics material is injected to fill these recesses. The injected material forms a collar which completely surrounds the tube. The bag film material on either side of the tube is melted to itself and to the tube wall, and the collar is securely attached in an encircling configuration so precluding leakage. The tube may be part of a tap or other outlet fitting such as a push-pull tap.

6 Claims, 7 Drawing Sheets

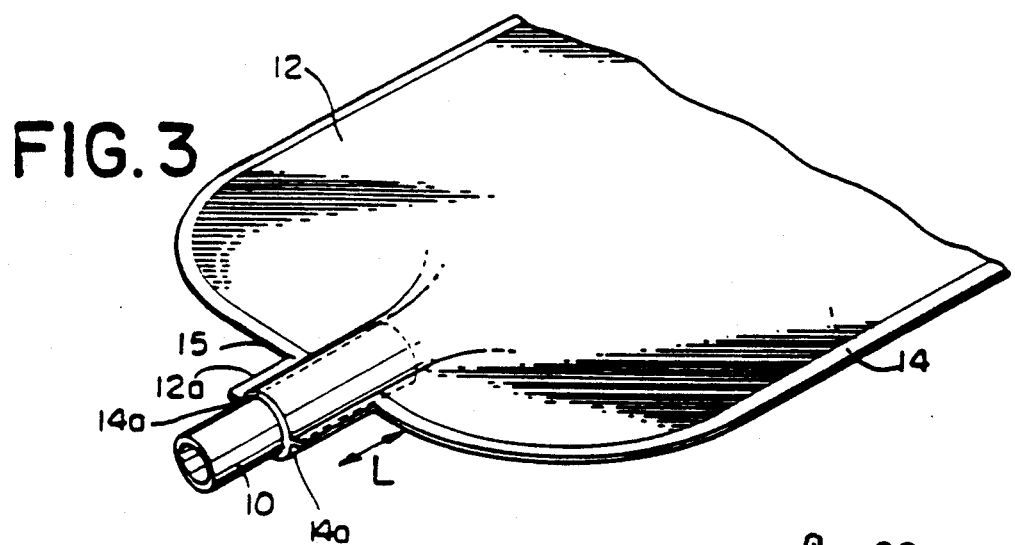
FIG.3
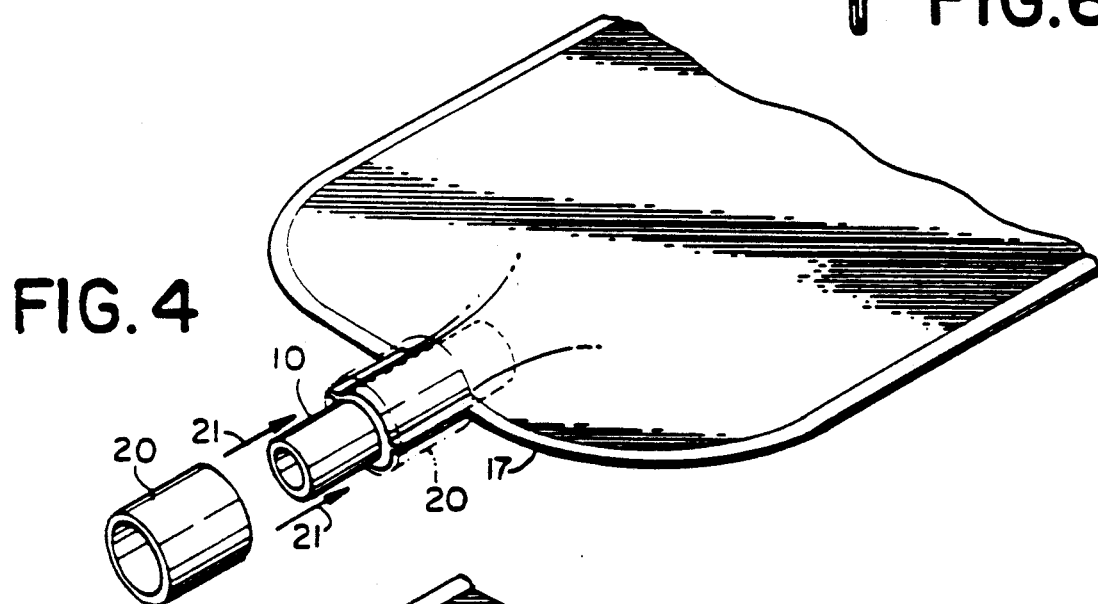
FIG.4
FIG.6
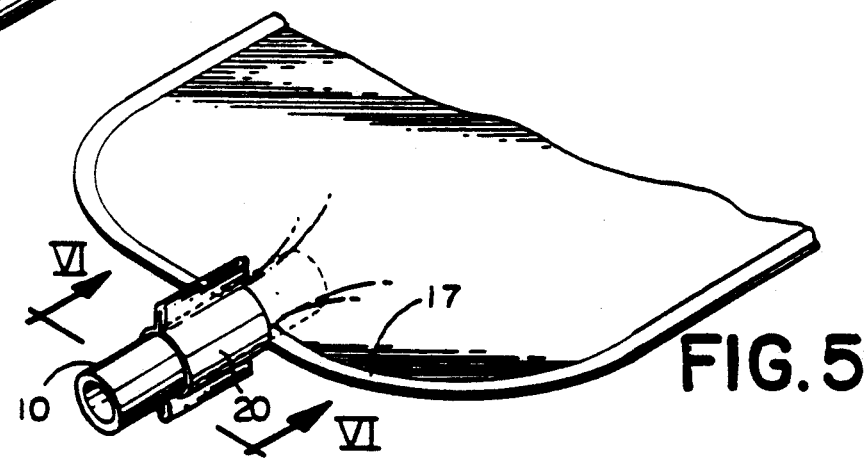
FIG.5

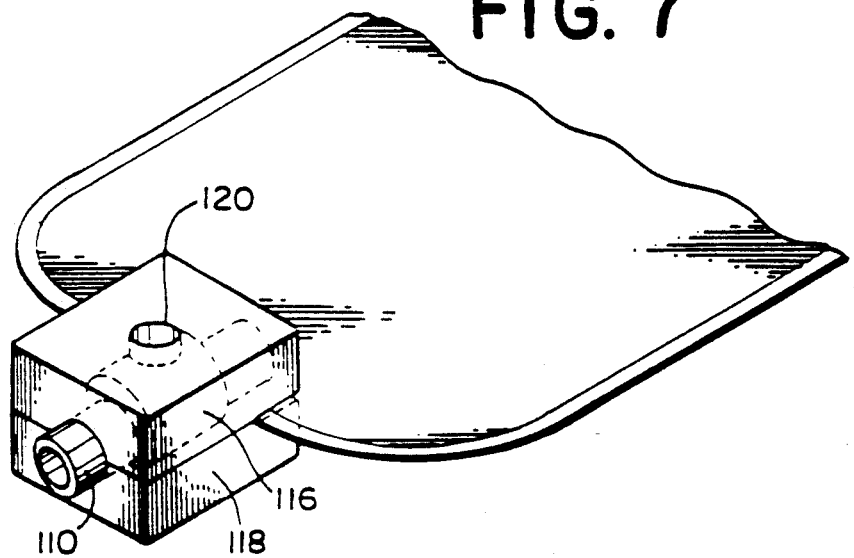
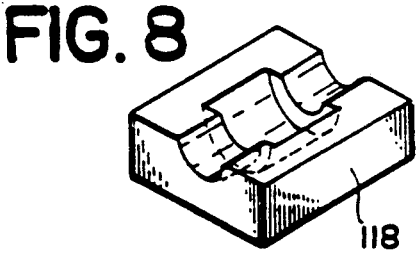
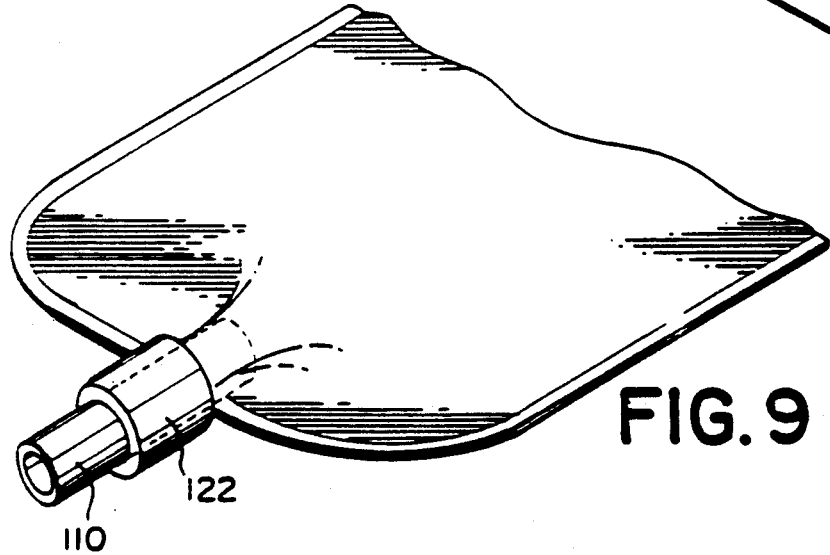

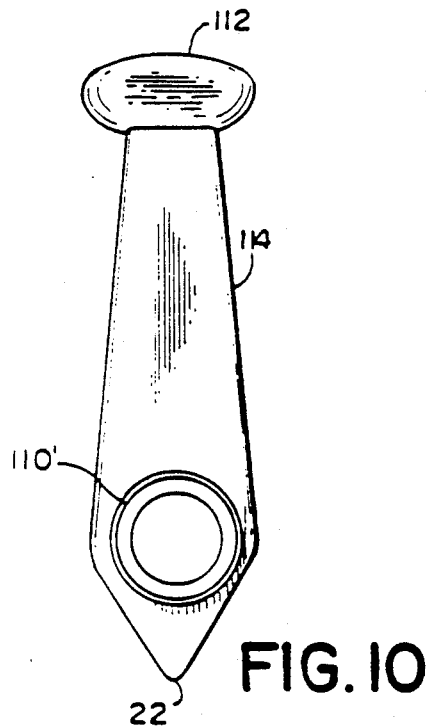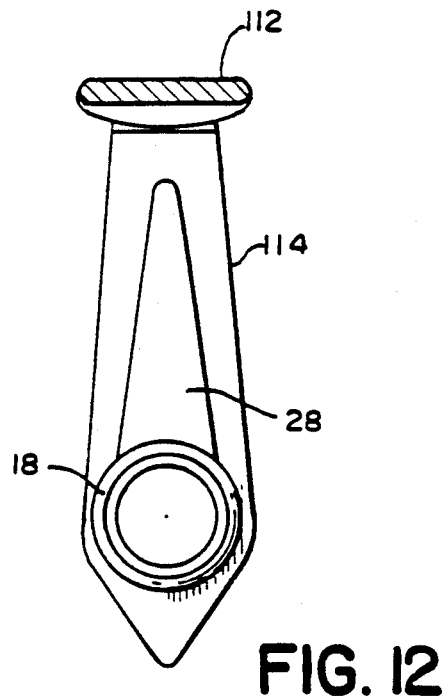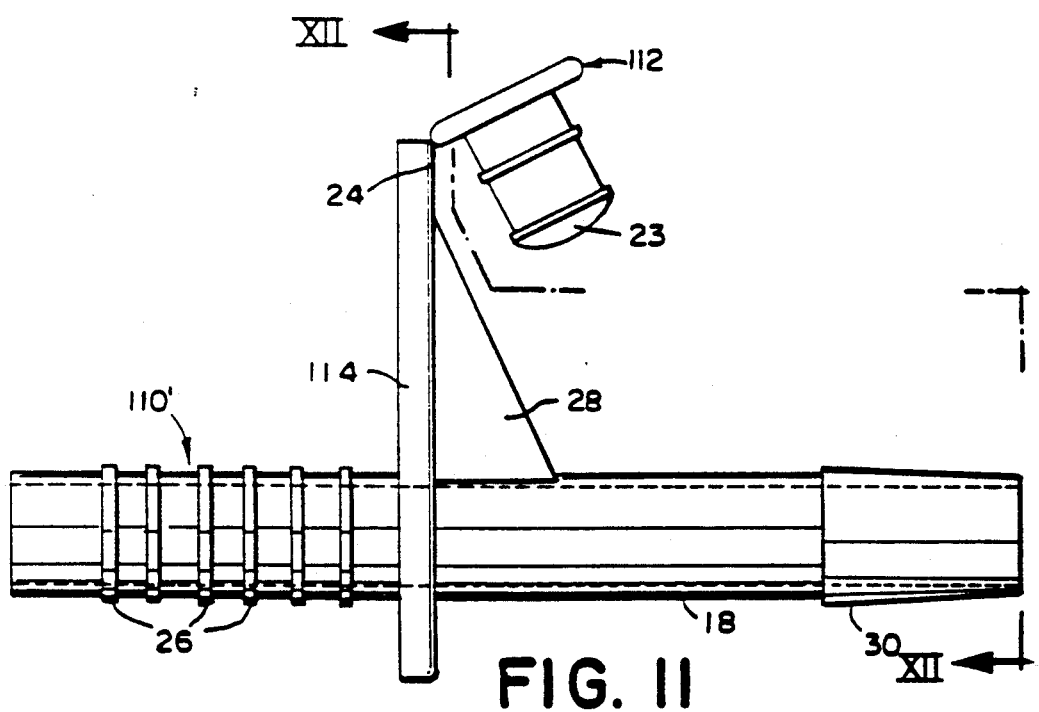

MANUFACTURE OF BAGS

This is a divisional application of application Ser. No. 07/374,415, filed Jun. 30, 1989, now U.S. Pat. No. 5,002,623 which is a division of application Ser. No. 215,835, filed Jul. 6, 1988, now U.S. Pat. No. 4,876,788, issued Oct. 31, 1989, which is a continuation-in-part of application Ser. No. 123,428, filed Nov. 20, 1987, now abandoned.

BACKGROUND OF THE INVENTION

This invention relates to the manufacture of bags for containing liquids, and to the bags themselves.

Bags such as urostomy bags, urine bags, colostomy bags, etc. are commonly made from two superposed sheets of plastic material welded around their periphery. The weld may be radio-frequency welding or heat welding. It is often desired to have an outlet tube from a lower region of the bag. Such tubes are often also plastic material. One proposal for heat welding a tube to a bag is shown in U.S. Pat. No. 4,023,607 of O. R. Jensen et al. Problems arise when making weld joints to fix the tube to the two bag walls in a leak-proof manner. In particular, there frequently exist two leak paths LP at the locations indicated in FIG. 2 of the accompanying drawings. This problem is particularly acute with bags for containing urine because urine has a low surface tension and will readily find any leak path. Welding a plastic tube between bag walls is a particularly difficult problem when one is employing multi-film laminate material for each bag wall, some of the layers of the laminate being intended to provide strength and liquid impermeability and one or more layers of the laminate being particularly directed to providing gas impermeability. In the contest of a rate of manufacture of bags of up to 2000 per hour, and using a thin multi-laminate bag wall, joining such a wall to a tube of appreciable wall thickness presents difficulties in delivering a suitable amount of heat both to the thin bag wall film and to the relatively thick tube wall.

SUMMARY OF THE INVENTION

According to the present invention, a bag for containing liquids and having an outlet tube is manufactured by a first step of seam welding the tube between two superposed bag walls, and by a subsequent step of sliding an encircling sleeve over the tube to a position where it contains within it the portions of the bags walls on either side of the tube, and, thirdly, compressing the sleeve onto the tube by crimping operation conducted with the crimping force applied in a direction radially of the tube, but at substantially right angles to the plane in which the bag wall lie.

In this method, one can employ a crimpable plastic sleeve, or a crimpable metal sleeve, or a composite sleeve made of both metal and plastic. The basis of this invention is that the application of crimping force in the direction indicated will cause the bag wall strips on either side of the tube to be compressed under high pressure towards and into the adjacent portion of the tube wall, which reduces the possibility of the leak paths LP being present in the manufactured product.

The invention also provides a bag for containing liquids in which a joint between an outlet tube and superposed portions of the bag walls is encircled by a sleeve crimped thereon in the manner described. In this way, it is possible in most cases to preclude any leak paths.

In an alternative embodiment of the invention, a tube is held in position between two superimposed walls of a bag by a light seam welding operation, without taking any special precautions, at this point, to make the joint leakproof. Thereafter, the bag and tube combination is placed between the blocks of a mold, each having confronting recesses of a particular shape, and molten plastic is injected to fill these recesses, the injection being done, as normal, under heat and pressure. The injected material forms a collar which completely surrounds the tube having been melted to itself and to the tube wall and the collar being securely attached in an encircling configuration to preclude leakage.

The invention accordingly provides a bag for containing liquids in which a joint between an outlet tube and superposed portions of the bag walls is encircled by a collar of moldable synthetic plastics material molded thereon under heat and pressure. In this way, it is possible in most cases to produce a bag outlet which does not have any leak paths.

In another aspect of the invention, a method for manufacturing a bag for containing liquids comprises the steps of seam welding an outlet tube in position between superposed bag walls and, as a second step, injection molding a collar of synthetic plastics material, chosen to be compatible with the bag walls and tube, around the tube, the collar being molded under heat and pressure so as to close off any leak paths.

The tube may be a part of any kind of tap or other outlet fitting.

According to a particular embodiment of the invention, a push-pull type tap is welded between the walls of a drainage or an ostomy bag.

BRIEF DESCRIPTION OF THE DRAWINGS

The invention will be better understood from the following description of non-limiting embodiment thereof given with reference to the accompanying drawings in which:

FIG. 3 illustrates the first step of one example of a method according to the present invention, in perspective view;

FIG. 4 illustrates a later step of the method in which a sleeve is placed in position for crimping;

FIG. 5 is a perspective view showing a crimped-on sleeve;

FIG. 6 is a cross-sectional view on the sectional plane VI—VI illustrating the completed bag having a crimped-on sleeve;

FIG. 7 is a perspective view of a bag with a tube inserted and a mold over the tube in the manner of an alternative embodiment of the invention;

FIG. 8 is a perspective view of a portion of the mold used in conjunction with the invention as illustrated in FIG. 7;

FIG. 9 is a perspective view of the completed bag made in accordance with the alternative embodiment of the invention;

FIG. 10 is an end view of a form of bag outlet which incorporates an integral stopper;

FIG. 11 is a front view of the outlet shown in FIG. 7;

FIG. 12 is a cross-section on the line XII—XII of FIG. 11.

DETAILED DESCRIPTION OF THE PREFERRED EMBODIMENT

Figure 1:
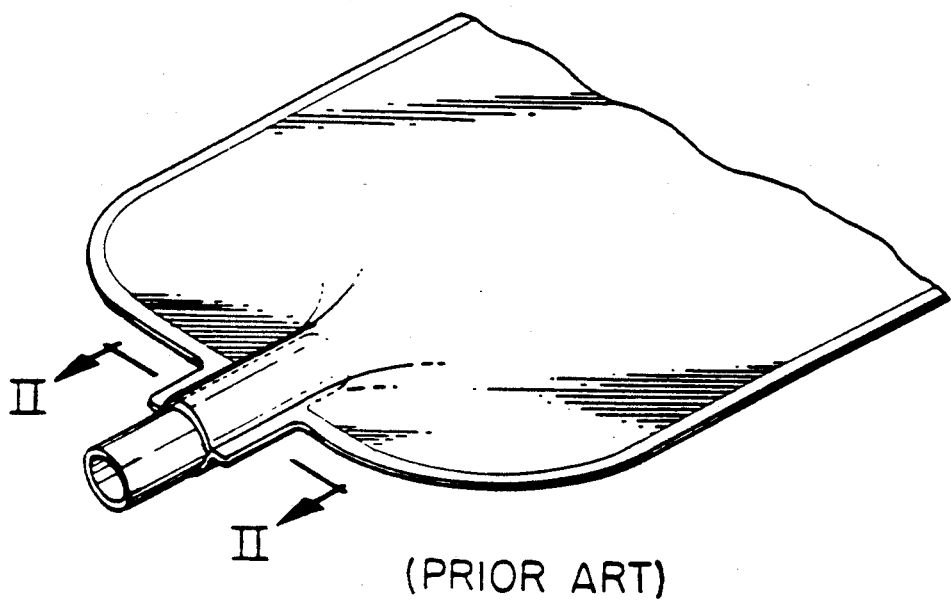
FIG. 1 is a perspective view of a bag having an outlet tube attached thereto in a conventional manner.

Referring to FIGS. 3–6, in the method according to the invention, the tube 10 is lightly seam welded by the illustrated seam weld 15 between the two superposed bag films 12 and 14. This weld joint may be quickly made as it is not necessary that the joint be leak-proof. Its purpose is to hold the parts in position during the next step. A crimpable sleeve 20, e.g., of metal or plastic material, is then placed over the tube and pushed towards the bag (as indicated by arrows 21) so that the sleeve surrounds the parts 12a, 14a, of the superposed bag walls and one end of the sleeve lightly abuts the edge 17. Using a conventional crimping tool, and applying the crimping force in a direction substantially at 90 degrees to the plane of the bag walls, the sleeve is next crimped tightly onto and over the tube and the wall portions 12a, 14a. Because the force is applied in the indicated direction, the material of the sleeve is forced under high pressure towards those region of the bag wall material adjacent to the leak paths LP and the sleeve when crimped forces this material into tight engagement with the exterior surface of the tube. At the end of crimping, the sleeve has taken up a permanent set and tightly holds the bag wall material now squashed out of strip form to close off the leak paths LP.

One advantage of the method particularly disclosed herein is that crimping being a fast operation, high productivity can be obtained without compromising quality.

In the present specification, a reference has been made to applying the crimping force at right angles to the plane of the walls of the bag. The purpose of this is to be sure of compressing the bag wall strips tightly against the tube. Angles other than 90 degrees could be used, e.g., an angle in the range of 75–90 degrees would be suitable in many cases, and the invention is considered to include this possibility.

Figure 2:
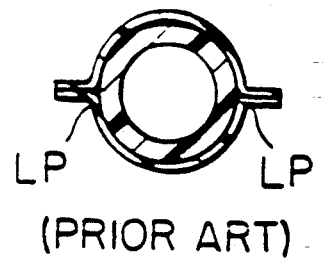
FIG. 2 is a cross-section on the line II—II of FIG. 1 illustrating the two leak paths LP which frequently occur with this (prior art) method despite all efforts to avoid them.

With reference to FIGS. 7–9, an alternative embodiment of the present invention is illustrated. In the alternative embodiment, a plastic tube 110 is lightly seam welded between the two superposed bag films 12 and 14 in a manner similar to that described for FIGS. 3–6. The tube may itself be an injection molded tube and may be ribbed. As a second step, the intermediate product so produced is placed between two mold blocks 116 and 118, FIG. 7, whose shape can be seen from FIG. 8. The upper block 116 has an injection port 120 for entry of synthetic plastic material and the remaining portions of the injection molding apparatus are not shown since they are conventional and will be familiar to a man of average skill in this art. The mold blocks 116 and 118 are shaped to define an encircling collar which extends axially of the tube length substantially equal to the length 1 indicated in FIG. 3. In the second stage of the manufacturing method, molten synthetic plastics material which is compatible with the tube material and the bag film material is injected through the hole 120 under heat and pressure. Polyethylene, particularly high density polyethylene, is suitable. For use with some film materials containing or made of e.v.a., it may be desirable to use for the injected plastics material a plastics a material which includes up to 10% of e.v.a. to obtain compatibility with the bag film. The skilled man in the art will naturally choose suitable materials in the light of the bag film being used. Temperatures and pressures conventionally employing in injection molding the chosen plastics material are suitable in this instance. The injected material is then allowed to cool and the blocks are opened. During the cooling, the collar shrinks, which reduces the likelihood of leak paths being formed. The resulting product is illustrated in FIG. 9. As will be seen, an out collar 122 is molded around and integrated with the material of the tube 110 and the portions 12a, 14a, (FIG. 3) of the bag film material. Due to the application of heat and pressure during the injection molding step, the likelihood of the resulting product having leak paths such as leak paths LP of FIG. 2 is greatly reduced.

Referring now to FIGS. 10–12, the illustrated bag outlet tube 110 suitable for use with FIGS. 7–9 includes an integral stopper 112. The tube 110 is made in one piece with a bag wall attachment block 114, a web 28 and an outlet portion 18. The latter is flexible so that the tube 18 can be folded up and its open end engaged with the stopper 112 whereby an obturating member 23 of the stopper 112 closes the outlet end of the tube portion 18.

The attachment block 114 has a shape as seen in plan which tapers sharply to one end 22 of the block and tapers less sharply to the other end of the block. At this end of the block 114 there is a relatively stiff, integral connection 24 to the stopper 112. This permits a slight amount of flexing of the stopper relative to the block 114. The tube 110 has peripheral ribs 26 on its outer surface in the region above the block 114; these assist in securing good adhesion without leakage when the bag walls are united with the outlet in the manner described above. The web 28 is provided integral with the block 114 and the tube outlet portion 18 to prevent undesired flexing of the portion of the tube 18 near to the block 114. A tapered fitting 30 is integral with the outlet portion 18.

Figure 13:
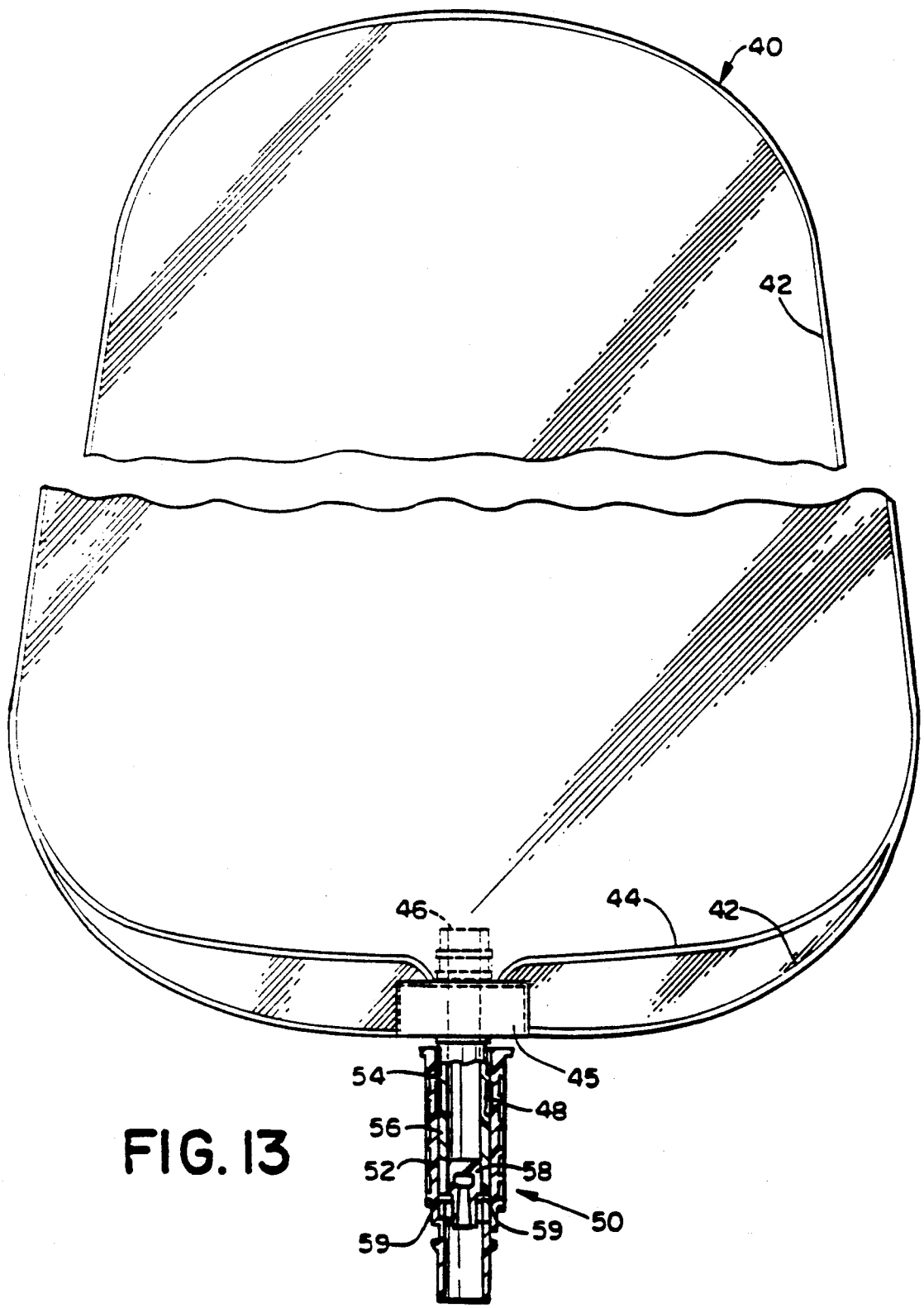
FIG. 13 is a front view of a drainage bag including a welded-in push-pull type outlet tap.
Figure 14:
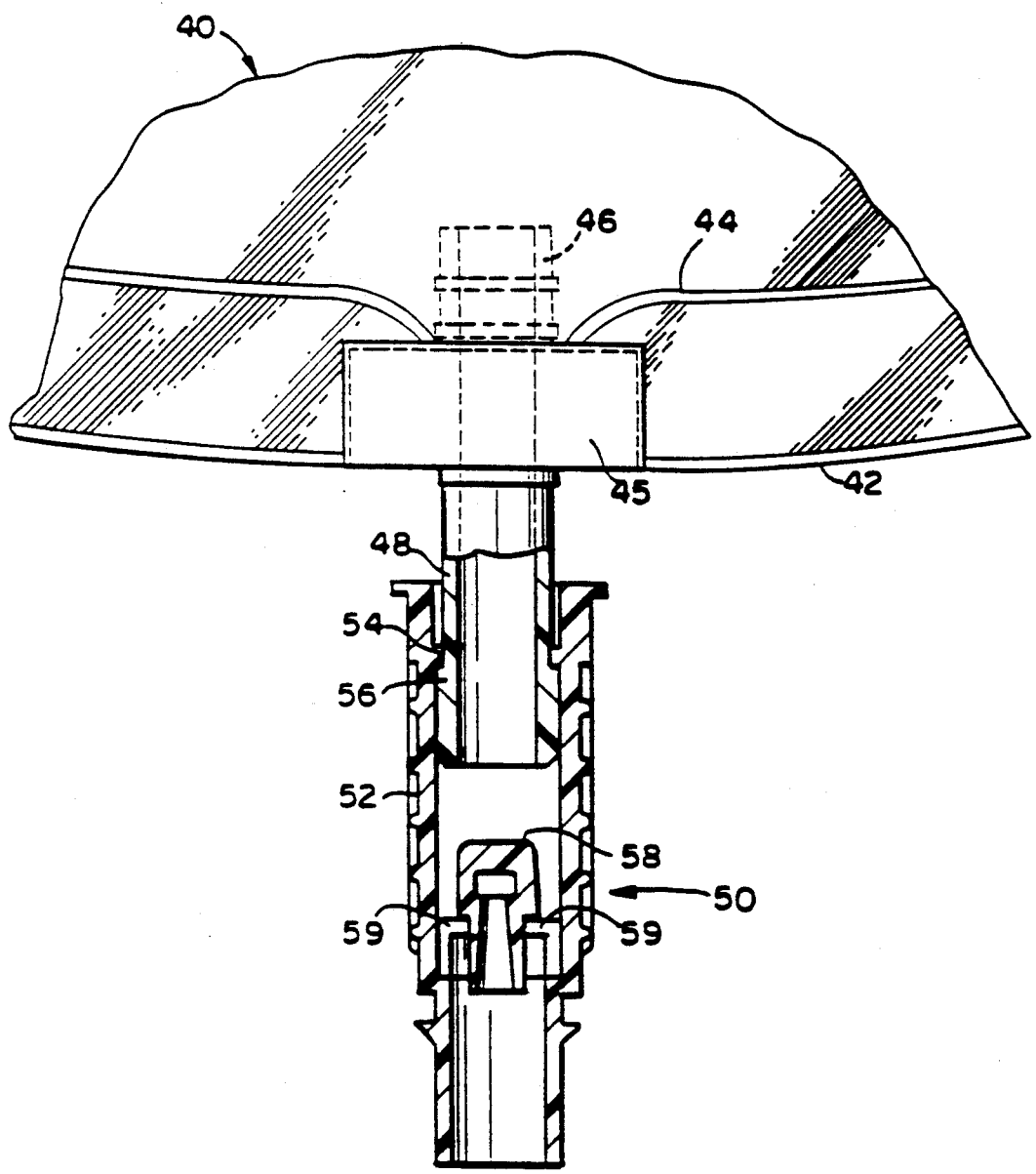
FIG. 14 is a view similar to FIG. 10 but showing the outlet tap in its open (pulled down) condition.

FIGS. 13 and 14 illustrate a different embodiment of the invention. A bag 40 for receiving urine has front and rear walls welded together around the periphery by welds 42 and 44. At the outlet region between the walls is indicated a block 45 which is tapered suitably to merge with the walls, as is known in the art (see for example British Patent No. 1 308 519 now expired). The block 45 is made integral with a first tube 46 and a second tube 48 which forms the inner member of a push-pull tap 50. The movable member of the tap 50 is generally identified 52 and is axially slidable relative to the tube 48. The lower limit of this axial sliding movement is determined, as best seen in FIG. 14, by engagement of an internal flange 54 on the tube 52 with a peripheral rib 56 on the tube 48. This defines the open condition of the tap 50. The upper limiting (closed) condition of the tap 50 occurs when an obturating member 58 mounted internally within the tube 52 by radial arms 59 (in spider fashion) is in engagement with the lower end of the tube 48 and stops the urine escaping from within the bag. Suitable guide means (not shown) are provided to ensure that the tube 52 slides truly axially relative to the tube 48 but the sizing and engagement of the parts is chosen so that the friction is sufficient to keep the tap normally closed.

This kind of tap is readily integrated with a bag in the same operation by which the walls of the bag are welded together. This leads to a considerable reduction in the cost of manufacture and yet yields a virtually leakproof bag having an integral tap. While a push-pull tap has been illustrated, in FIGS. 13 and 14 other kinds of tap can be employed with equal or greater advantage. The integration achieved by the disclosed method between the parts 42, 44, 45 and 46 is such that the difficult problem of leakage in this area is almost 100% overcome.

Figure 15:
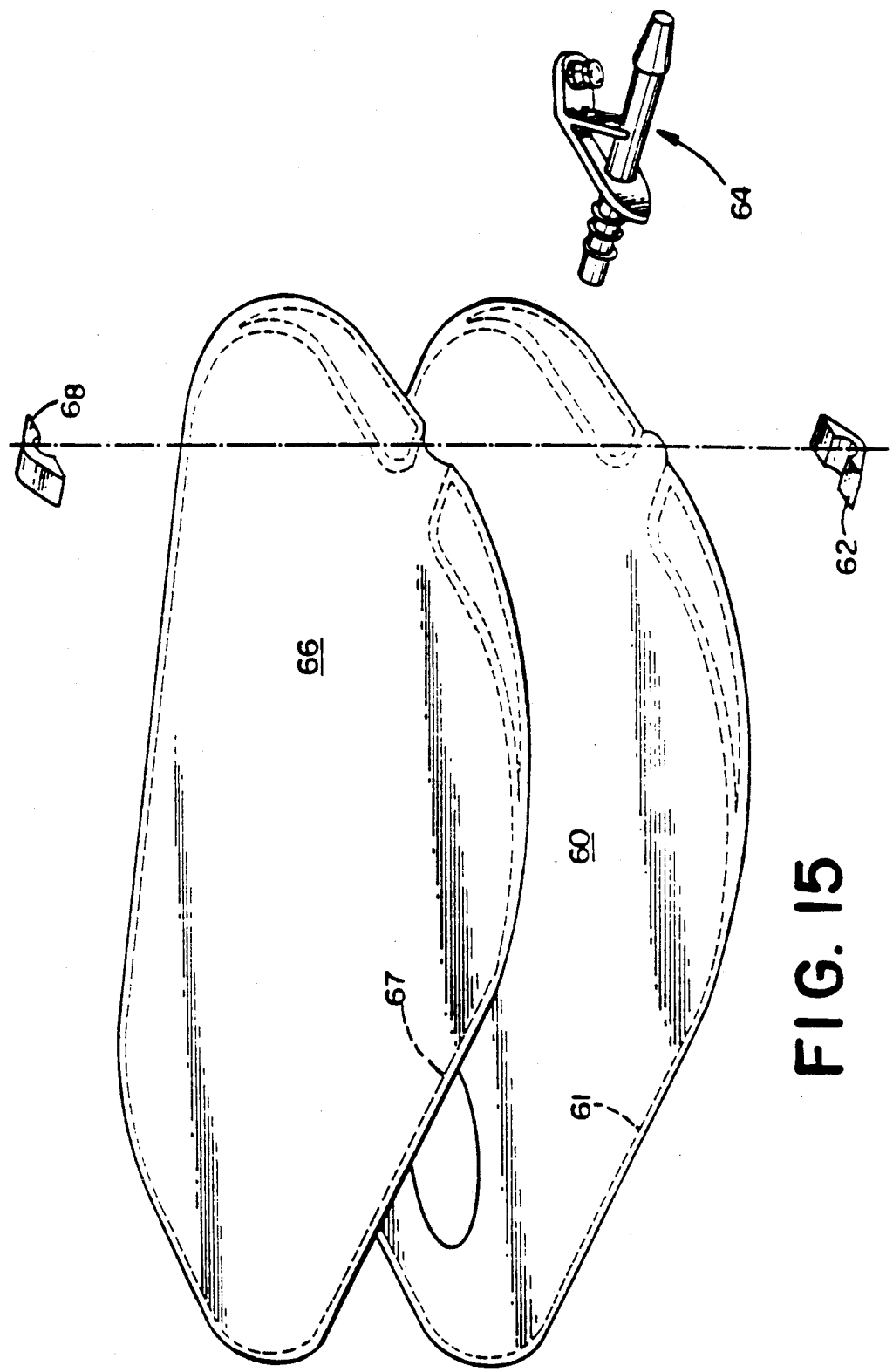
FIG. 15 is a perspective view illustrating an embodiment of the invention.

FIG. 15 illustrates a step in a preferred assembly method in accordance with the invention. An ostomy bag rear wall formed by a film 60 is laid in a suitable injection molding machine on top of a shaped block 62. An outlet means 64 (which may be in accordance with FIGS. 10-12 or FIGS. 13 and 14 but is illustrated as a simple spigot having an integral plug) is placed in an appropriate location on the film 60. A front wall formed by a film 66 is then laid over. Finally a block 68, similar to block 62 is placed on the film 66 above the outlet means 64. The blocks 62 and 68 are of synthetic plastics material compatible with that of the film and the outlet means 64. A seam welding step is then carried out to bond together the peripheries of the films 60, 66 at the seams indicated 61, 67, and to trap the outlet means 64 therebetween. Reliance is not placed on this operation to achieve a leakproof joint between the outlet means 64 and the films 60, 66. Thereafter, an injection molding operation is carried out, under the application of heat and pressure, to bond securely together the parts even numbers 60–68. The resulting ostomy bag is found to be free of leaks, due to the thorough unification of the parts 60, 62, 64, 66 and 68 by the disclosed method.

We claim:

1. A bag for containing fluids comprising:
   a pouch for receiving fluids, said pouch having a rear pouch wall and a superposed front pouch wall, said pouch having a bottom through which said fluid may be outletted;
   a tube-shaped outlet tap at said pouch bottom, said outlet tap having a portion overlapped by said pouch walls and a portion extending externally to said bag walls;
   a crimped sleeve encircling at least part of said overlapped portion so as to capture a portion of said pouch walls between said sleeve and said outlet tap, said sleeve having two crimps, each located at angles of 75-90 degrees to said pouch wall, said sleeve being crimped with sufficient force to close off any leak path at the junction of said outlet tap and pouch walls, said outlet tap being openable to outlet liquid therefrom and closable so as to contain fluid within said pouch.

2. The bag of claim 1 further comprising a stopper coupled to said outlet tap, said outlet tap having a flexible outlet portion with an open end, said outlet portion being foldable so as to dispose said open end to be engagable by said stopper.

3. The bag of claim 1 wherein said outlet tap includes an attachment block integrally molded therewith, and a stopper is attached to said block, said stopper being capable of closing said outlet tap.

4. The bag of claim 1 wherein said outlet tap includes an attachment block and said outlet tap includes a web integral with said outlet tap for preventing undesired flexing of said outlet tap.

5. The bag of claim 1 wherein said outlet tap includes a push-pull tap.

6. The bag of claim 1 wherein said outlet tap includes peripheral ribs on its outer surface.

* * * * *